United States Patent [19]

Tovey et al.

[11] 4,029,880

[45] June 14, 1977

[54] LABELLED DERIVATIVES OF STEROIDS

[75] Inventors: Keith Charles Tovey, Amersham, England; John William Addison Findlay, Research Triangle Park, N.C.

[73] Assignee: The Radiochemical Centre Limited, England

[22] Filed: June 19, 1975

[21] Appl. No.: 588,165

[30] Foreign Application Priority Data

June 20, 1974 United Kingdom ............ 27510/74

[52] U.S. Cl. .................................. 536/7; 424/182
[51] Int. Cl.² ........................................ C07J 17/00
[58] Field of Search ..................... 260/210.5; 536/5

[56] References Cited

UNITED STATES PATENTS 3,925,355  12/1975  Piasio ............................ 260/210.5

*Primary Examiner*—Lewis Gotts
*Assistant Examiner*—Cary Owens
*Attorney, Agent, or Firm*—Wenderoth, Lind & Ponack

[57] ABSTRACT

Radio-iodine derivatives of digoxin and digitoxin are provided having the formula IV, where
 R is H or lower alkyl
 n is 1, 2 or 3
 Y is H or carboxyl
 m is 0 to 5, and
 Q is a phenolic or imidazole ring,
to which radio-iodine atoms are attached. Novel intermediates in the preparation of the radio-iodine derivative are described. The derivatives are useful for the radioimmunoassay of digoxin and digitoxin.

11 Claims, No Drawings

LABELLED DERIVATIVES OF STEROIDS

This invention relates to new derivatives of digoxin and digitoxin and a method for their preparation. Further, the invention relates to radioisotopically labelled derivatives of digoxin and digitoxin and their use in competitive radio-assay.

The cardiac glycosides (digoxin and digitoxin) are widely used in the therapy of certain disturbances of cardiac rhythm. The dosage must be carefully controlled as levels above those which show optimal therapeutic effect can be seriously toxic. It has been shown that the accurate measurement of cardiac glycosides in serum or plasma is most conveniently accomplished by radioimmunoassay. Smith et.al. (New England Journal of Medicine vol. 281, pages 1212–1216 (1969)) have published a method for determining digoxin levels in serum by the use of $^3$H-digoxin. However, the use of iodinated cardiac glycosides avoids the problems associated with the liquid scintillation counting of $^3$H compounds. Further, the relatively low specific activity of $^3$H-cardiac glycosides requires relatively large sample volumes and longer counting times in order to attain the required sensitivity and reproducibility in the assay.

It is an object of this invention to provide derivatives of the cardiac glycosides, and means for making such derivatives, which are either radio-iodinated or are suitable for radio-iodination and subsequent use in radioimmunoassay procedures. The present invention accordingly provides compounds represented by the following structural formula

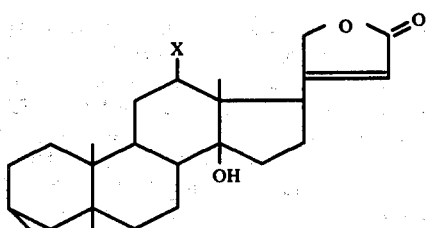

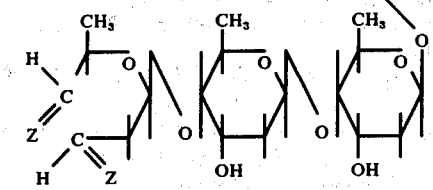

wherein one or two groups Z are $= NO(CHR)_n \cdot CO \cdot R_1$, any remaining group Z being $= O$;
X is —OH or —H;
R is H or $C_1$ to $C_4$ alkyl;
n is 1, 2, or 3;
$R_1$ is either —OH or —NH·CHY·$(CH_2)_m$ Q;
Y is —H or —$COOR_2$;
m is 0, 1, 2, 3, 4, or 5;
$R_2$ is H, $CH_3$ or $C_2H_5$;

Q is unlabelled or labelled and has one of the following structural formulae:

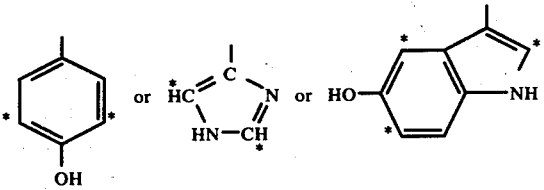

and the symbol * indicates the probable positions at which the compound may be labelled with one or more radioactive iodine atoms.

When X is —OH, the compounds are derivatives of digoxin. Whe X is —H, the compounds are derivatives of digitoxin.

When $R_1$ is —OH, the compounds are novel intermediates in the production of the desired radio-iodinated derivatives. They may be prepared by the steps of:

a. oxidizing digoxin or digitoxin to the dialdehyde, e.g. by means of sodium periodate; and b. reacting the dialdehyde with an o-carboxyalkoxylamine having the formula $NH_2 \cdot O(CHR)_n \cdot COOH$, where R and n are as defined above, to form a mono- or di- o- carboxyalkyloxime derivative thereof. The use of o-carboxymethoxylamine (R is H, n is 1) is preferred. The resulting oxime derivative can be reacted by formation of a peptide bond with any of a wide range of amines including amino acids. If the amine has a phenolic or imidazole ring, the product can readily be radio-iodinated, for example using sodium iodide and chloramine-T, to provide the desired labelled derivative of digoxin or digitoxin. Provided it has a phenolic or imidazole ring, the nature of the amine is not critical to this invention. For example, the amine may be one of the following

| | Y | m | Q |
|---|---|---|---|
| Histamine | —H | 1 | |
| Histidine | —COOH | 1 | |
| Histidine ethyl ester | —$COOC_2H_5$ | 1 | |
| Tyrosine | —COOH | 1 | |
| Tyrosine methyl ester | —$COOCH_3$ | 1 | |
| -(4-hydroxyphenyl)-ethylamine | —H | 1 | |

The reaction scheme can be represented as follows, where D represents digoxigenin (or digitoxigenin) didigitoxoside:

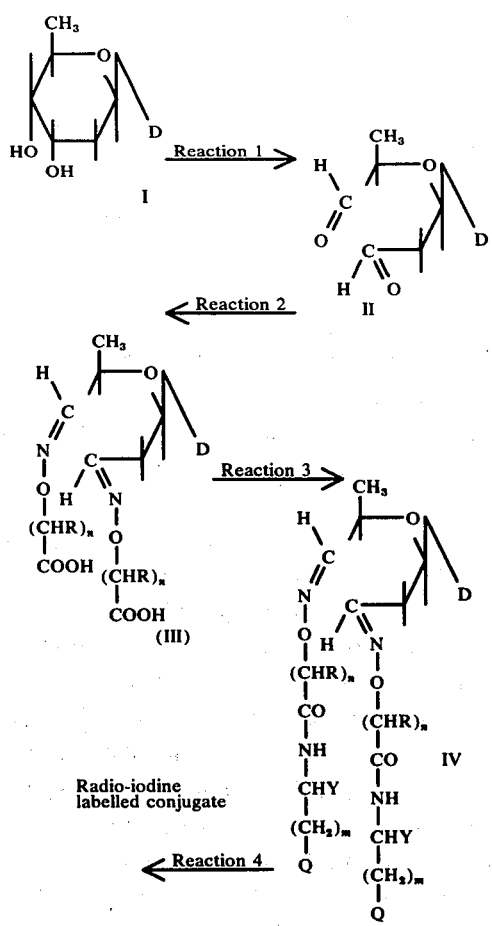

There follows a description of the preferred process according to the invention.

REACTION 1.

The oxidation of digoxin (or digitoxin) to the dialdehyde is effected with sodium periodate. The reagent splits 1:2 glycols and one molecule of periodate is used for each pair of adjacent alcohol groups. In carbohydrate chemistry the oxidation is normally carried out in water but still takes place rapidly in aqueous ethanol or aqueous dioxan solutions when water-insoluble compounds are being oxidized. The reaction is normally carried out at room temperature and may be carried out in the light. In the case of digoxin (or digitoxin) the reaction is complete within 30 minutes under these conditions. It is presumed that the product of the oxidation is the dialdehyde although by analogy with the work of Guthrie and Honeyman (J. Chem. Soc., 2319 (1959)) it is possible that in solution the dialdehyde is in equilibrium with the hemialdal:

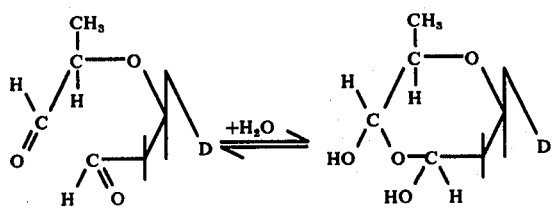

The dialdehyde is extracted with ethyl acetate and the solvent is removed by vacuum distillation to leave a white solid.

REACTION 2

The dialdehyde is condensed with o-caroxymethoxylamine to form the di-O-carboxymethyloxime (possibly together with some mono-oxime). (We envisage that other O-carboxyalkoxylamines would be effective if they were ever to become available).

Oximes are normally prepared by warming the carbonyl compound in aqueous or aqueous alcoholic solution with an aqueous solution prepared from hydroxylamine or a derivative and a molar equivalent of sodium hydroxide, sodium carbonate or sodium acetate. Under these conditions the oxime often separates. Alternatively, the oximination is carried out in the presence of rather more than two moles of aqueous alkali. However, we have shown that the dialdehyde is very unstable in weak alkali at room temperature. For example, in aqueous ethanol solutions adjusted to pH 9 with potassium carbonate, the dialdehyde is quantitatively converted to a compound with a lower $R_F$ (thin layer chromatography on silica gel in $CHCl_3$:methanol, 9:1) which no longer contains a reactive carbonyl group (i.e. it will no longer form an oxime). Therefore, to form the oxime of digoxin of digitoxin dialdehyde it is generally preferable to operate at a pH below 9.

Generally, the yield of the oxime derivative of a steroid is dependent on the initial molar ratio of O-carboxymethoxylamine: steroid. We have obtained reaction yields of close to 100% using a molar ratio of about 5.

REACTION 3

This stage involves the formation of a peptide bond between carboxylic acid groups of the O-carboxymethyloxime and the amino groups of the previously mentioned amine or amino acid radicals. Facile preparation of a peptide derivative may be achieved through the action of one equivalent of an N,N'-substituted carbodiimide on a solution containing an equivalent of an amino compound and an equivalent of a carboxylic acid. If the acid salt of the amino compound is used, one equivalent of a tertiary base is also added. The reaction proceeds with the formation of an equivalent of an N,N'-disubstituted urea derivative which may or may not precipitate from solution, depending upon the type of N,N'-disubstituted carbodiimide employed as well as the nature of the solvent used for the reaction. The formation of the peptide bond is usually carried out at temperatures ranging from 4° to 28° C., in an inert organic solvent although aqueous mixtures can also be employed.

In the current preparation dicyclohexylcarbodiimide is used as the condensing agent although several of the newer carbodiimides which incorporate tertiary or quaternary amine substituents may also be used such as 1-cyclohexyl-3-(morpholinylethyl)carbodiimide, its metho-p-toluenesulphonate derivative and 1-ethyl-3(3-dimethylaminopropyl)carbodiimide.

REACTION 4

The radioiodination procedure is based upon a method similar to that of Greenwood, Hunter and Glover, Biochemical Journal 89 114 (1963).

Oxidation of the $Na^{125}I$ is accomplished with chloroamine T. The quantity of chloroamine T must be sufficient to neutralize the small amount of reducing agent present in the Na$^{125}$I as well as to oxidise the I$^-$. Iodination is generally carried out in a small volume (~0.2 ml final) in 0.1 to 0.5 M borate or phosphate buffer pH 7.5 to 8.5 at 0°–28° C. The reactionis allowed to proceed for 1–10 minutes following which excess sodium metabisulphite is added to stop the reaction.

The I125-antigen is purified after iodination to remove free iodie and other reactants. The purification maybe carried out by ion-exchange gel filtration on a molecular sieve such as Sephadex G 25 and/or thin layer chromatography on silica gel.

The invention also includes a method of performing a competitive radio-assay for digoxin or digitoxin by the steps of a. causing the digoxin or digitoxin to compete with a standard amount of radioactively labelled digoxin or digitoxin for reaction with a specific reagent therefore present in a standard amount insufficient to bind all the labelled and unlabelled compound;

b. separating the bound compoun from the unbound compound; and c. measuring the proportion of radioactivity in at least one of the bound and the unbound compound, characterized in that the radioactively labelled digoxin or digitoxin is an amine conjugate of a digoxin or digitoxin dialdehyde bis-o-carboxyalkyl oxime as herein described.

EXAMPLE 1

The preparationof digoxin-TME labelled with 125I.

As digoxin and digitoxin differe by one one —OH group on C 12 of the steroidal moeity of the molecule it is not considered necessary to describe an example for the preparation of labelled digoxin. However, tyrosine methyl ester (TME) conjugates of both digoxin dialdehyde bis-o-carboxymethyloxime and digitoxin dialdehyde bis-o-carboxymethyloxime have been prepared. NMR data obtained from a sample of the latter derivative, which confirms the general structure of these compounds, is given below.

218 mg of digoxin were dissolved in 12 ml of boiling 78% ethanol. The solution was allowed to cool to room temperature and 214 mg of sodium periodate dissolved in 7 ml of water were added. The solution was allowed to stand for 30 minutes at room temperature before the addition of 0.3 ml of ethylene glycol. The reaction mixture was evaporated to small volume (~5 m) and the volume adjusted to 15 ml with water. The solution was extracted three times with 15 ml of ethyl acetate and the combined organic layers were backwashed with water. The extract was evaporated almost to dryness by rotary evaporation at 30° C., and finally taken completely to dryness after the addition of diethyl ether to give a white solid. The product was analysed by thin layer chromatography on silica gel developed with chloroform:methanol, 9:1 (system A). The compound was visualised by sulphuric acid charring. A single spot with an R$_F$ of 0.54 was observed.

273 mg of carboxymethoxylamine hemihydrochloride and 250 mg of sodium acetate were dissolved in 1.2 ml of distilled water. 196 mg of periodate cleaved digoxin in 7.6 ml of ethanol were added to this solution. The reaction mixture was refluxed for 1 hour and then evaporated to about 0.5 ml. The volume was adjusted to 5 ml with water and the solution extracted four times with 5 ml of ethyl acetate. The combined organic layers were backwashed with water. The extract was evaporated almost to dryness at 30° C., and finally taken completely to dryness after the addition of diethyl ether. Analysis of the product of the reaction by thin layer chromatography on silica gel developed with system A showed complete reaction of the dialdehyde to give a product which remained at the origin. The oxime had an RF of 0.16 after thin layer chromatography on silica gel developed with chloroform:acetone-acetic acid, 7:2:1.

180 mg of the di-O-carboxymethyloxime were dissolved in a mixture of 3.6 ml of dioxane and 0.36 ml of water which contained 91 mg of TME hydrochloride, 81 mg of dicyclohexylcarbodiimide and 75 mg of tri-n-butylamine. The solution was kept at 4° C., for 24 hours. Thin layer chromatography on silica gel in system A showed a major product with an R$_F$ of 0.58 (digoxin had an R$_F$ of 0.39 in this system) which was visualised both by sulphuric acid charring and ferric chloride colour reaction.

After preparative thin layer chromatography on 1.0 mm silica gel plates, developed with system A, the band corresponding to the TME-derivative was eluted with ethyl acetate. The solvent was removed by evaporation at 30° C. The amorphous residue was homogeneous on thin layer chromatography (silica gel plates, solvent methanol:chloroform, 6:94 v/v).

The NMR spectrum as measured on the digitoxin conjugate, for example, shows that the ratio of tyrosine methyl ester to cardenolide in these conjugates is 2. The NMR spectrum was recorded at a frequency of 100 MHz in CDCl$_3$. Chemical shifts and integration are in agreement with the proposed structure (IV in scheme I). The ratio of the integral for the aromatic proton to that for the olefinic proton (in the genin) indicates two tyrosine methyl ester radicals per molecule.

| Protons | Chemical Shift Observed (δ)* | Characteristics |
|---|---|---|
| Aromatic | 6.89 | doublet |
| Aromatic | 6.70 | doublet |
| Lactone | 5.86 | singlet |
| Methyl ester | 3.74 | singlet |
| Methyl ester | 3.72 | singlet |
| Angular CH$_3$ | 0.87 and 0.91 | singlets |

*ppm with respect to tetramethylsilane as internal reference.

Radioiodiniation of the TME-conjugate of digoxin was effected with carrier-free Na$^{125}$I in an aqueous ethanol solution containing chloramine-T. The pH of the solution was about 7.5. The reaction time varies from 1–10 minues. After the addition of excess sodium metabisulphite the reaction mixture was chromatographed on 0.25 silica gel plates in system A. The radioactive bands were eluted with ethyl acetate or ethanol. The radioiodinated TME-conjugate was stored at −20° C in 50% ethanol prior to use as the labelled antigen in the radioimmunoassay of digoxin.

EXAMPLE 2

The Radioimmunological Assay of Digoxin

The assay was carried out in polystyrene or glass tubes using the following reagents:

i. 0.05 M potassium phosphate buffer pH 7.4 containing 0.15 M sodium chloride, 0.5% bovine serum albumin and 0.01% thiomersal. All subsequent reagents were diluted in this buffer except (iv) and (v).

ii. antiserum (rabbit) to digoxin at a dilution which bound about 60% of the added radioactive digoxin.

iii. digoxin tyrosine methyl ester conjugate labelled with $^{125}$I at approximately 2 ng/ml. (Satisfactory assay curves were still obtained with this solution after 28 days storage at 37° C).

iv. normal human serum (digoxin-free, zero standard)

v. standard digoxin in normal human serum at concentrations of 0.5, 1.0, 2.0, 4.0 and 8.0 ng/ml.

vi. Norit GSX charcoal suspended in phosphate buffer as above.

vii. Human serum containing unknown concentration of digoxin.

The assay procedure was as follows.

Duplicate tubes were prepared for totals, blanks (which contain no antiserum), the standards and unknown serum samples. 0.1 ml of the zero standard was added to all tubes. 1.1 ml of the phosphate buffer was added to the totals and 0.1 ml to the blank. 0.1 ml of the radioactive digoxin was added to all tubes followed by the addition of 0.1 ml of the standards and unknowns to the appropriate tubes. 0.1 ml of antiserum was added to all tubes except totals and blanks. All tubes were mixed on a vortex mixer and incubated at room temperature for 30 minutes. Then 1 ml of the charcoal suspension (stirred magnetically) was added to all tubes except the totals. The tubes were mixed on a vortex mixer and allowed to stand at room temperature for 5 minutes. All tubes were subsequently centrifuged at 2,000 g for 5 minutes, the supernatants were decanted into polystyrene tubes. The radioactivity of the bound fraction in the supernatant was measured in a well-type γ-counter.

The following results were obtained from the standards:-

| Digoxin Concentration (ng/ml) | % Radioactivity bound. |
|---|---|
| 0 | 60 |
| 0.5 | 48 |
| 1.0 | 40 |
| 2.0 | 30.5 |
| 4.0 | 22 |
| 8.0 | 15 |

From these figures a calibration curve can be drawn, off which the digoxin concentration of the unknown sample can easily be read.

We claim:

1. A compound having the structural formula

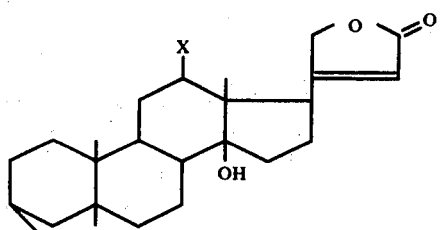

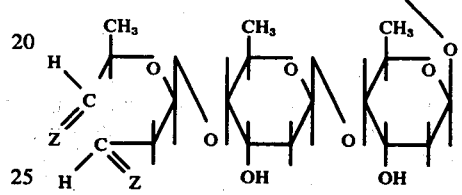

wherein one or two groups Z are $=NO(CHR)_n CO \cdot R_1$, any remaining group Z being = 0;

X is —OH or —H;
R is H or $C_1$ to $C_4$ alkyl;
n is 1, 2 or 3;
$R_1$ is either —OH or —NH·CHY·$(CH_2)_m$Q;
Y is —H or —COOR$_2$;
m is 0, 1, 2, 3, 4 or 5;
$R_2$ is H, CH$_3$ or $C_2H_5$;
Q is unlabelled or labelled and has one of the following structural formulae:

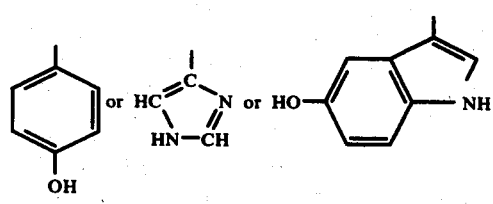

2. A compound as claimed in claim 1, wherein
R is H;
n is 1; and
$R_1$ is —OH.

3. A compound as claimed in claim 1, wherein
R is H;
n is 1;
$R_1$ is —NH·CHY·$(CH_2)_m$Q;
m is 1; and
Q is

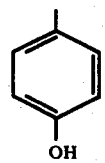

4. A compound as claimed in claim 1, labelled with one or more 125-iodine atoms.

5. A compound as claimed in claim 4, wherein
X is H;
R is H;
n is 1;
$R_1$ is $-NH\cdot CH(CO\cdot OCH_3)CH_2Q$
Q is

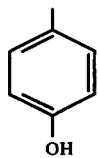

6. A compound as claimed in claim 4, wherein
X is OH;
R is H;
n is 1;
$R_1$ is $-NH\cdot CH(COOCH_3)\ CH_2Q$;
Q is

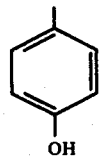

7. A process for making a compound as claimed in claim 1, wherein $R_1$ is $-OH$, which process consists essentially of
 a. oxidising digoxin or digitoxin to the dialdehyde;
 b. reacting the dialdehyde with an o-carboxyalkoxyamine having the formula

where r and n are as defined in claim 1, to form a mono- or di-o-carboxyalkyloxime derivative thereof.

8. A process for making a compound as claimed in claim 1 wherein $R_1$ is $-NH\cdot CHY\cdot (CH_2)_mQ$, which process consists essentially of the steps:
 a. oxidising digoxin or digitoxin to the dialdehyde;
 b. reacting the dialdehyde with an o-carboxyalkoxylamine having the formula

where R and n are as defined in claim 1, to form a mono- or di-o-carboxyalkyloxime derivative thereof,
 c. reacting the resulting oxime derivative by formation of a peptide bond, in the presence of an N,N'-substituted carbodimide, with an amine having the formula $NH_2\cdot CHY\cdot (CH_2)_mQ$, where Y, m and Q are as defined in claim 1, to form an amine conjugate thereof.

9. A process as claimed in claim 8, comprising the additional step of radio-iodinating the resulting amine conjugate.

10. In a method of performing a competitive radioassay for digoxin or digitoxin by the steps of
 a. causing the digoxin or digitoxin to compete with a standard amount of radioactively labelled digoxin or digitoxin for reaction with a specific reagent therefor present in a standard amount insufficient to bind all the labelled and unlabelled compound,
 b. separating the bond compound from the unbound compound; and
 c. measuring the proportion of radioactivity in at least one of the bound and the unbound compound, the improvement wherein the radioactively labelled digoxin or digitoxin is an amine conjugate of a digoxin or digitoxin dialdehyde bis-o-carboxyalkyl oxime having the structural formula

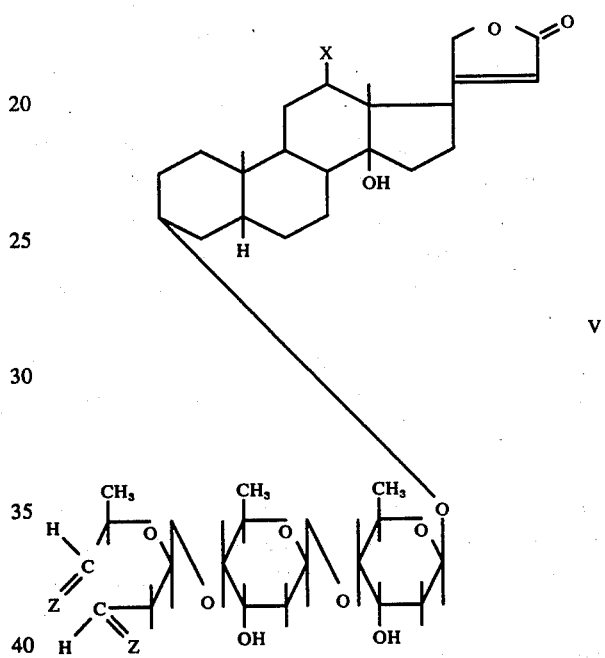

wherein one or two groups Z are $=NO(CHR)_n CO\cdot R_1$, any remaining group Z being $= O$;
X is $-OH$ or $-H$;
R is H or $C_1$ to $C_4$ alkyl;
n is 1, 2 or 3;
$R_1$ is either $-OH$ or $-NH\cdot CHY\cdot (CH_2)_mQ$;
Y is $-H$ or $-COOR_2$;
m is 0, 1, 2, 3, 4 or 5;
$R_2$ is H, $CH_3$ or $C_2H_5$;
Q is unlabelled or labelled and has one of the following structural formulae:

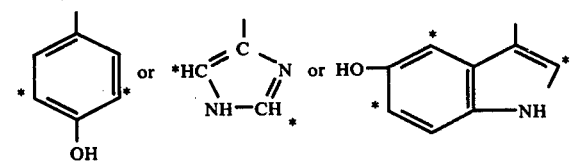

11. A method as claimed in claim 10, wherein the radioactive labelled digoxin or digitoxin is a compound is labelled with one or more $I^{125}$ atoms.